United States Patent
Martinez (10) Patent No.: US 11,166,841 B1
(45) Date of Patent: Nov. 9, 2021

(54) SNORING AND SLEEP APNEA PREVENTION DEVICE AND METHODS

(71) Applicant: Lubin Martinez, Orange, CA (US)

(72) Inventor: Lubin Martinez, Orange, CA (US)

(*) Notice: Subject to any disclaimer, the term of this patent is extended or adjusted under 35 U.S.C. 154(b) by 0 days.

(21) Appl. No.: 17/163,009

(22) Filed: Jan. 29, 2021

(51) Int. Cl.
*A61F 5/56* (2006.01)
*A61B 13/00* (2006.01)

(52) U.S. Cl.
CPC .............. *A61F 5/566* (2013.01); *A61B 13/00* (2013.01)

(58) Field of Classification Search
CPC ... A61F 5/566; A61F 5/56; A61C 7/36; A61B 13/00; A61M 16/04; A61M 16/0495
See application file for complete search history.

(56) References Cited

U.S. PATENT DOCUMENTS

| | | | |
|---|---|---|---|
| 3,132,647 A | 5/1964 | Corniello | |
| 5,718,575 A * | 2/1998 | Cross, III | A61F 5/566 433/6 |
| 5,983,892 A | 11/1999 | Thornton | |
| 6,766,801 B1 | 7/2004 | Kerpian | |
| 6,769,910 B1 | 8/2004 | Patino | |
| 7,770,582 B2 | 8/2010 | Chen et al. | |
| 8,302,609 B2 | 11/2012 | Martinez | |
| 10,772,757 B1 * | 9/2020 | Harris | A61F 5/566 |
| 2006/0130850 A1 * | 6/2006 | Chen | A61F 5/566 128/848 |
| 2008/0041396 A1 | 2/2008 | Lucker | |
| 2009/0241969 A1 * | 10/2009 | Walker | A61F 5/566 128/848 |
| 2012/0073581 A1 * | 3/2012 | Martinez | A61F 5/566 128/848 |
| 2012/0145166 A1 * | 6/2012 | Fallon | A61F 5/566 128/848 |
| 2013/0125902 A1 * | 5/2013 | Danielian | A61F 5/566 128/859 |
| 2015/0230970 A1 * | 8/2015 | Kaner | A61F 5/566 128/848 |
| 2018/0200103 A1 * | 7/2018 | Keropian | A61B 13/00 |

* cited by examiner

*Primary Examiner* — Jacqueline T Johanas
*Assistant Examiner* — Shannel Nicole Belk
(74) *Attorney, Agent, or Firm* — Stout, Uxa & Buyan, LLP; Donald E. Stout (57) ABSTRACT

A mouth appliance for maintaining effective airflow in a user's airway comprises a frame formed to engage the user's upper and lower teeth to retain the frame in a selected position in the user's mouth in accord with the user's natural bite. A tongue depressor is mounted to the frame and formed to extend to a rear portion of the user's throat and to exert pressure directly on the tongue in the area of the user's soft palate, thereby facilitating comfort and ease in occasional swallowing, while providing airflow effectiveness to prevent the user from snoring and experiencing sleep apnea.

14 Claims, 7 Drawing Sheets

SNORING AND SLEEP APNEA PREVENTION DEVICE AND METHODS

FIELD OF THE INVENTION

This invention relates generally to an apparatus and method for treating and preventing, or at least alleviating, snoring and sleep apnea. More particularly, this invention relates to a device that a person may place in their mouth to restrain the tongue in such a manner as to prevent it from closing the airway as the person relaxes and falls asleep. The invention is particularly intended to be used to treat Obstructive Sleep Apnea (OSA) and/or severe snoring.

BACKGROUND OF THE INVENTION

The dangers of snoring and sleep apnea are well known. For example, untreated sleep apnea and chronic snoring can increase the risk of high blood pressure, heart attack, stroke, obesity, diabetes, atrial fibrillation, motor vehicle accidents, joint arthroplasty, metabolic syndrome, Parkinson's Disease, and dementia. There are surgical procedures and various devices that are used to treat snoring and sleep apnea, such as the commonly used CPAP (Continuous Positive Airway Pressure) machines. However, these prior art devices and methods are typically lacking in effectiveness, comfort, or both. More comfortable, easy to use, effective treatments are urgently needed for this increasingly common problem.

SUMMARY OF THE INVENTION

The present invention is an inexpensive orthodontic appliance for preventing the tongue and other tissues of a sleeping person from collapsing into his or her airway, and is an improved version of the appliance disclosed in Applicant's prior U.S. Pat. No. 8,302,609, herein expressly incorporated by reference, in its entirety. An appliance according to the present invention comprises a frame formed and fitted to the wearer's (or user's) natural bite, to engage the user's upper and lower teeth to retain the frame in a selected position in the user's mouth. The appliance further comprises a tongue depressor mounted to the frame and adapted to extend to a rear portion of the user's throat and exert pressure on the tongue in the area of the user's soft palate, thereby facilitating comfort and ease in occasional swallowing, while providing airflow effectiveness to prevent the user from snoring and experiencing sleep apnea.

The inventive appliance has a hard-exterior acrylic form, but with a softer inner lining, of a material that conforms to the user's teeth and natural bite at the point of contact, when worn. This softer material affords more comfort and ease of use, but also has a stabilizing effect when the oral appliance is worn.

Advantageously, the inventive appliance provides a new and effective solution for treating obstructive sleep apnea and chronic snoring. No surgery is required, nor does the inventive system tether the user to an obtrusive and unattractive face mask. The appliance can be worn comfortably for an entire night. The appliance does not trigger the gag reflex because it never touches any part of the throat. The tongue retaining mechanism is mounted on a pivot, thereby allowing the user to swallow during the night, after which it returns to its stationary position to keep the airway open without waking the user.

Additionally, the present invention does not project the jaw forward, thereby eliminating the associated joint pain common to devices of this nature.

The innovative tension mechanism utilized in the inventive system holds the tongue depressor in a forward stationary position during sleep. The tongue depressor effectively cradles the tongue in a forward position, thus maintaining an open airway for the user during sleep. The tension mechanism also functions as a pivoting bar for the tongue depressor. The tension/pivoting bar mechanism allows the user to swallow at night without waking or discomfort. The tension/pivoting mechanism then gently returns the tongue to the forward position, thus maintaining an open airway throughout the user's sleep.

In one particular aspect of the invention, there is provided a mouth appliance for maintaining effective airflow in a user's airway, which comprises a frame adapted to engage the user's upper and lower teeth to retain the frame in a selected position in the user's mouth in accord with the user's natural bite, the frame having left and right portions thereof. A flexible pivoting bar is mounted to the frame, the flexible pivoting bar being comprised of a shape memory material. A tongue depressor is connected to the pivoting bar and adapted to extend to a rear portion of the user's throat and exert forward pressure directly on the user's tongue in the area of the user's soft palate, thereby facilitating comfort and ease in occasional swallowing, while providing airflow effectiveness to prevent the user from snoring and experiencing sleep apnea symptoms. Advantageously, first and second portions of the flexible pivoting bar extend along and from corresponding ones of the left and right portions of the frame, the first and second portions of the flexible pivoting bar each extending from the frame and being secured to the tongue depressor.

In exemplary embodiments, the first and second portions of the flexible pivoting bar are formed into their corresponding ones of the left and right portions of the frame. This forming may be by injection molding or 3-D printing, for example. The flexible pivoting bar may comprise Nitinol, or other suitable shape memory material.

A clamp bracket is provided for securing the flexible bar to the tongue depressor, the clamp bracket comprising channels for receiving distal portions of the flexible pivoting bar therein and a fastener for securing the clamp bracket to the tongue depressor, to thereby secure the distal portions of the flexible pivoting bar to the tongue depressor. In some embodiments, the distal portions of the flexible pivoting bar comprises a plurality of notches, the plurality of notches being configured to engage with a plurality of notches disposed on a cover plate comprising a portion of the clamp bracket. The plurality of notches disposed on the distal portions of the flexible pivoting bar may comprise exterior notches, and the plurality of notches disposed on the cover plate may comprise corresponding interior notches.

The distal portions of the flexible pivoting bar comprise a bar center portion having first and second leg portions. In some center-mount embodiments, the first and second leg portions extend along a majority of a total length of the tongue depressor. In other outside-mount embodiments, the first and second leg portions extend along only a small distal portion of a total length of the tongue depressor.

In some embodiments, a plurality of cross-bars extending between the left and right portions of the frame, and across each of the flexible metal bar and the tongue depressor.

The frame typically comprises a hard acrylic plastic, having a softer interior material, typically silicone, and being encased by a soft silicone-type material. The tongue depressor comprises a metal alloy or a hard plastic, and is encased by a soft silicone-type material.

In another aspect of the invention, the flexible pivoting bar is encased in the frame and in the tongue depressor and comprises portions thereof which extend along each of the left and right portions of the frame, and along a length of the tongue depressor. In an illustrated embodiment, the flexible pivoting bar comprises a single continuous piece, and the portions thereof which extend along each of the left and right portions of the frame comprise opposed ends of the flexible pivoting bar. The portions of the flexible pivoting bar which extend along the tongue depressor comprise a center length of the flexible pivoting bar, wherein the center length is curved so that two portions thereof are disposed in parallel along the length of the tongue depressor.

The invention, together with additional features and advantages thereof, may best be understood by reference to the following description taken in conjunction with the accompanying illustrative drawings.

DETAILED DESCRIPTION OF THE INVENTION

Referring now more particularly to the drawings, wherein like reference numerals designate identical or corresponding parts throughout the several views and embodiments, there is shown in FIGS. 1-6a one exemplary embodiment of the present invention. An oral appliance 10 comprises a frame 12, common in the dental and orthodontic industry, and configured from a user's upper and lower dental impressions, of a hard plastic acrylic known for such purposes. The frame 12 thereby conforms to the anatomical characteristics of the user's mouth. An interior portion 14 is comprised of a softer material, such as a silicone material, also common in the dental and orthodontic industry, which when heated and then fitted to the user's mouth conforms to the user's individual dental structure and natural bite, thus enhancing comfort and assisting in keeping the oral appliance 10 in place during sleep.

A tongue depressor 16 is provided, which has a purpose and design to provide comfort and maximum effectiveness for the unobstructed flow of air, thereby allowing for and promoting breathing through the mouth and nose during sleep. The tongue depressor 16 is affixed to left and right rear ends 12a, 12b, respectively of the frame 12, by means of a corrosion resistant flexible metal bar 18, which may be comprised of Nitinol or another suitable shape memory metal alloy. The flexible characteristics of the bar 18 provides the tension needed to return the user's tongue to its forward position after occasional swallowing by the user. The bar 18 also acts as a pivoting mechanism, allowing the user to swallow during sleep, and then returns the tongue to its original forward position without disturbing the user's sleep. The bar 18 is of a shape, contour, and angle, and is secured to the tongue depressor 16, as shown in FIGS. 1-6a, and as described herein.

The tongue depressor 16, in the illustrated embodiment, has a curvature which extends downwardly and slightly forwardly, and is comprised of a corrosion resistant material, such as a metal alloy or hard plastic. The tongue depressor 16 may be encased in a soft silicone-type material 20, thereby providing a comfortable support system at the contact point with the tongue, which basically cradles the tongue during sleep. The soft silicone encasement 20 may be replaced as needed, due to normal use or if damaged. The tongue depressor 16 does not exert pressure on the user's tongue until occasional swallowing occurs. The tongue depressor 16 pivots on the tension/pivoting bar 18 during swallowing, and then gently allows the tongue to return and rest on the tongue depressor 16. The combination of these features provides an unobstructed open airway for the user during sleep. The size and curvature of the tongue depressor 16 and the pivoting/tension bar 18 is determined by a dental professional according to the dental impressions taken.

The tongue depressor 16 is attached to the appliance frame 12 in an appropriate manner. As illustrated, the tongue depressor 16 has a clamp bracket 22 comprising an affixed dental screw and lock nut 23, for receiving a center portion 24 of the bar 18, which is shown with particular clarity in FIGS. 6 and 6a.

Figure 1:
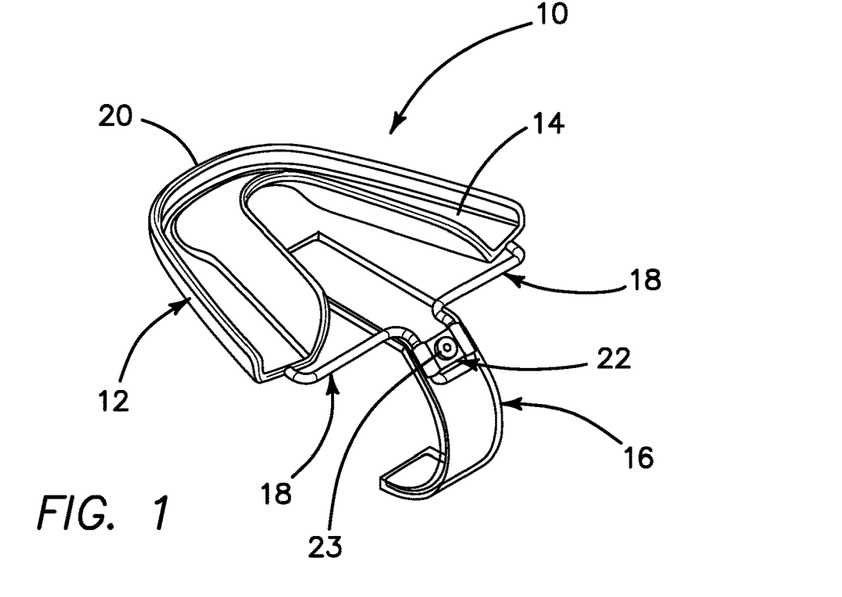
FIG. 1 is an isometric view of an exemplary embodiment of the present invention.
Figure 2:
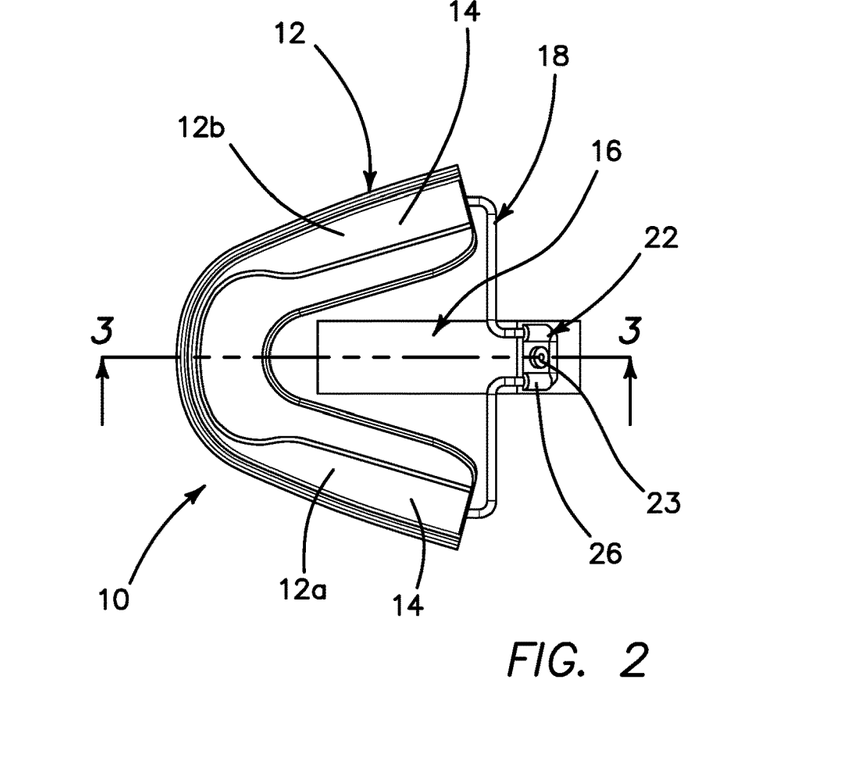
FIG. 2 is a top view of the embodiment shown in FIG. 1.
Figure 3:
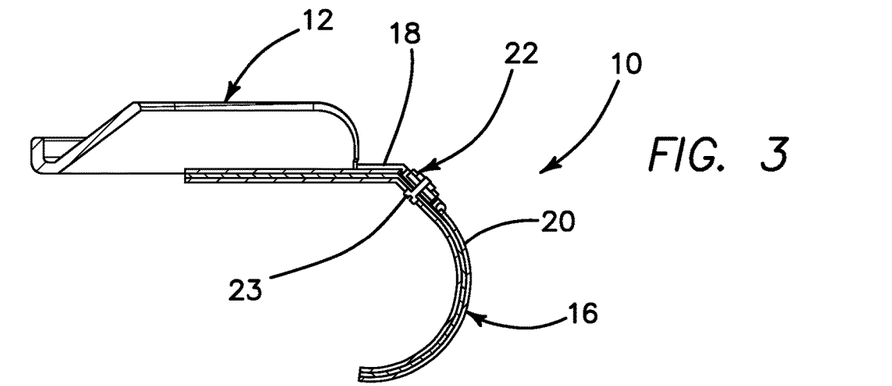
FIG. 3 is a cross-sectional view taken along lines A-A of FIG. 2.
Figure 4:
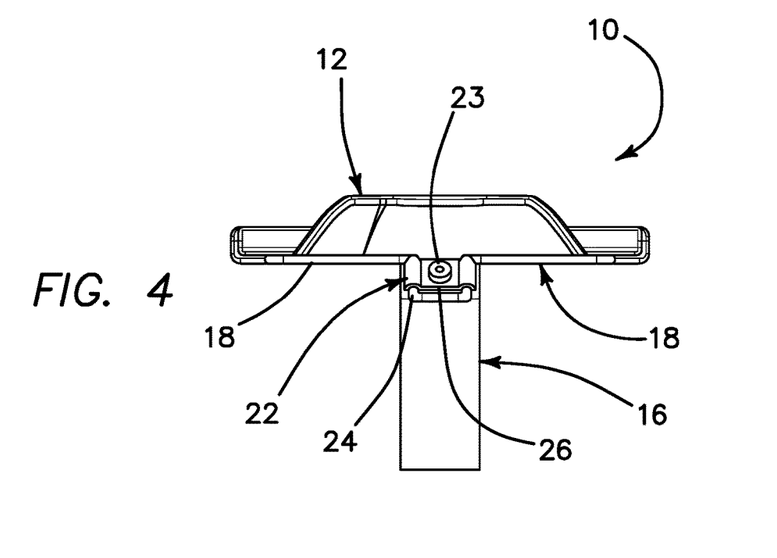
FIG. 4 is a rear view of the embodiment shown in FIGS. 1-3.
Figure 5:
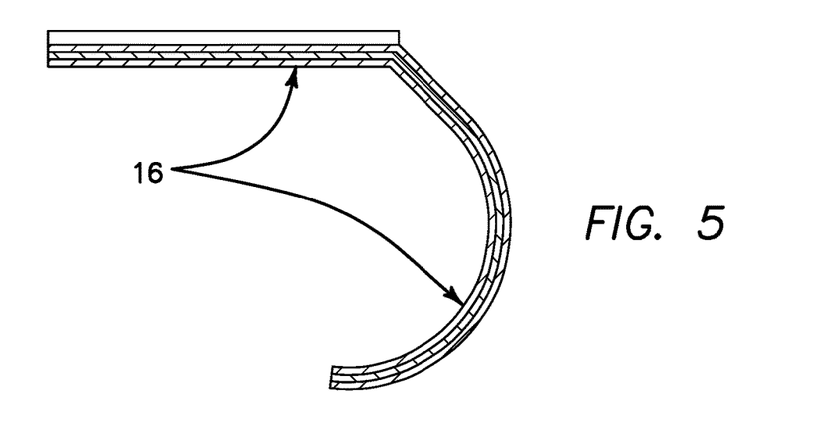
FIG. 5 is a cross-sectional view similar to FIG. 3, with the frame removed so that the tongue depressor is shown by itself.
Figure 5A:
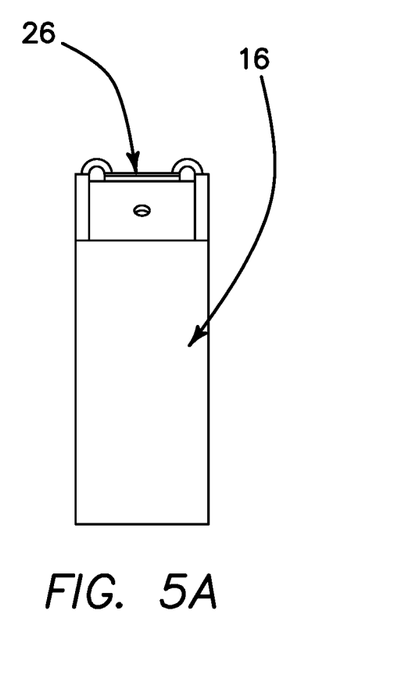
FIG. 5a is a rear view of the tongue depressor of FIG. 5.
Figure 6:
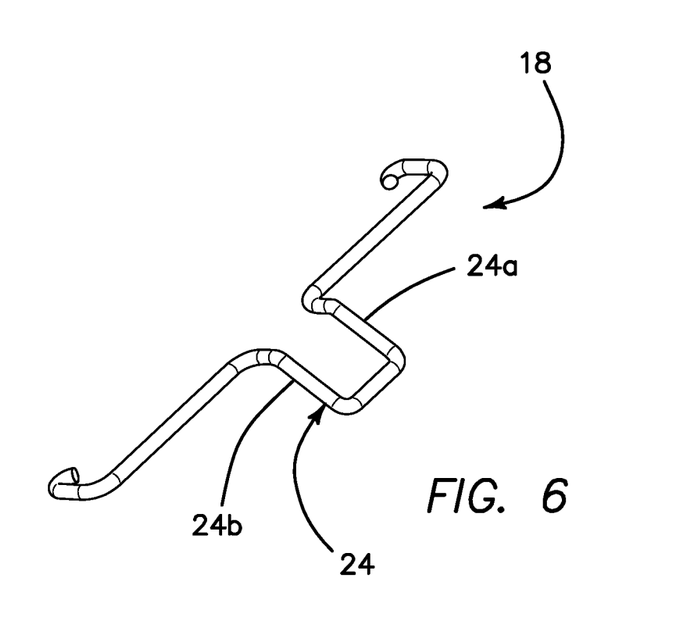
FIG. 6 is an isometric view of one exemplary embodiment of the flexible metallic bar of the present invention.
Figure 6A:
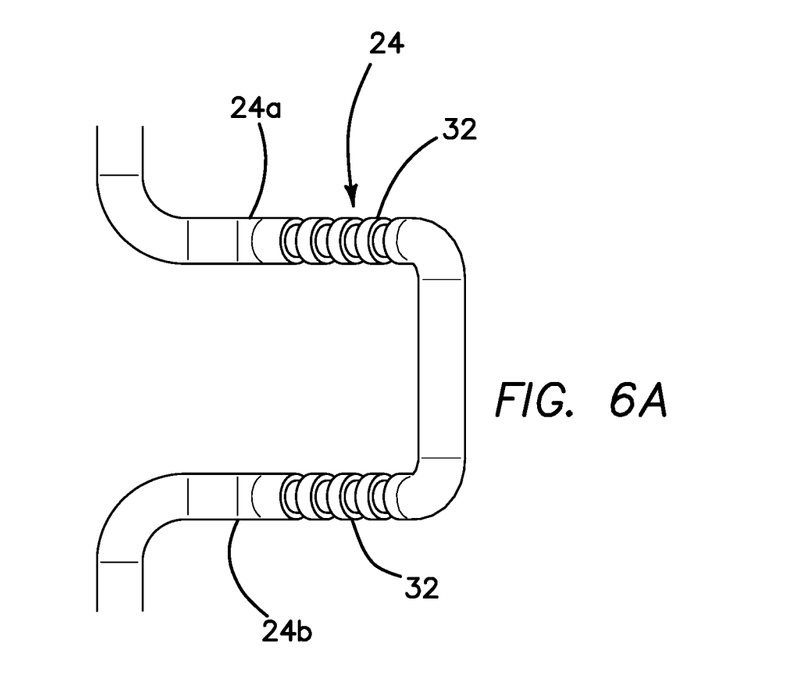
FIG. 6a is an enlarged view of a portion of the flexible metallic bar of FIG. 6.
Figure 7:
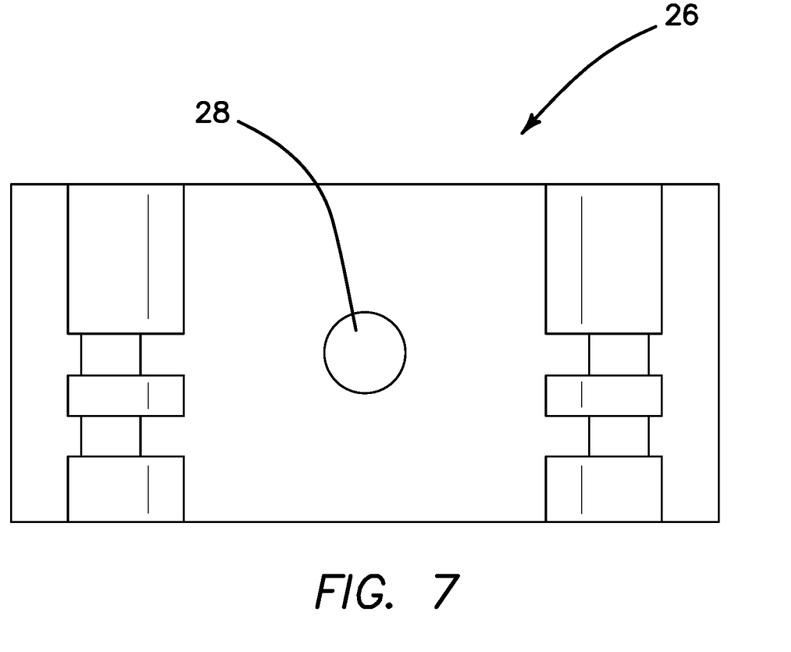
FIG. 7 is a top view of a cover plate usable with the exemplary embodiment of FIG. 1.
Figure 8:
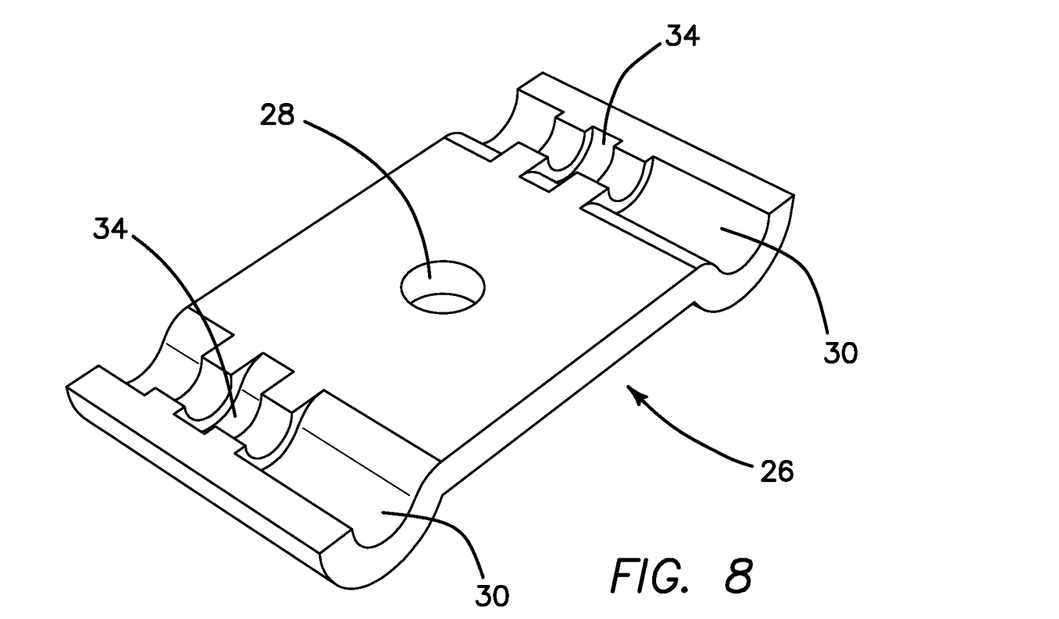
FIG. 8 is a bottom view of the cover plate shown in FIG. 7.
Figure 9:
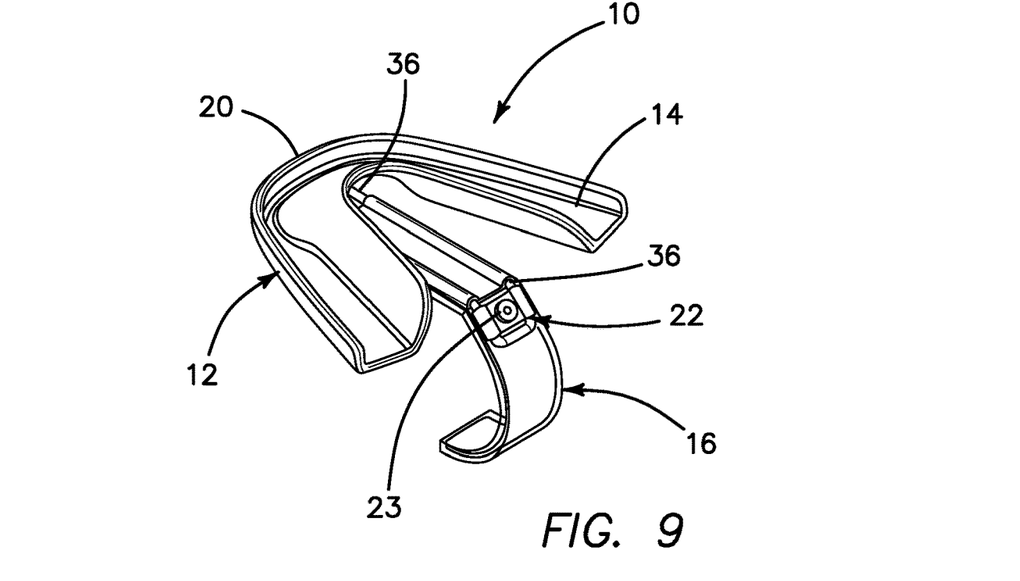
FIG. 9 is an isometric view of a modified exemplary embodiment of the flexible bar for the present invention.
Figure 10:
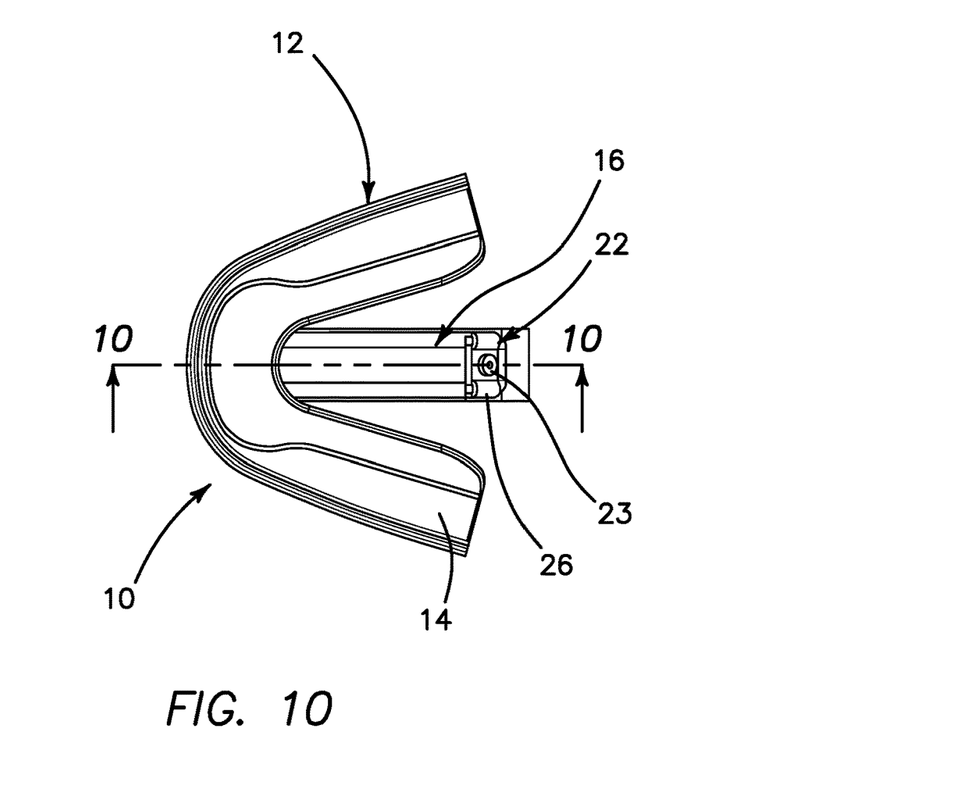
FIG. 10 is a top view of the embodiment of FIG. 9.
Figure 11:
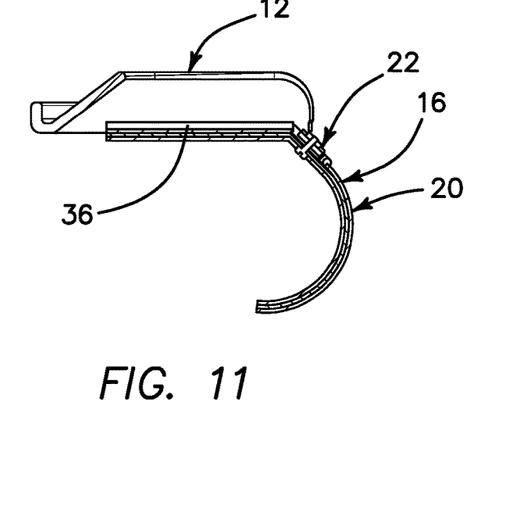
FIG. 11 is a cross-sectional view taken along lines A-A of FIG. 10.
Figure 12:
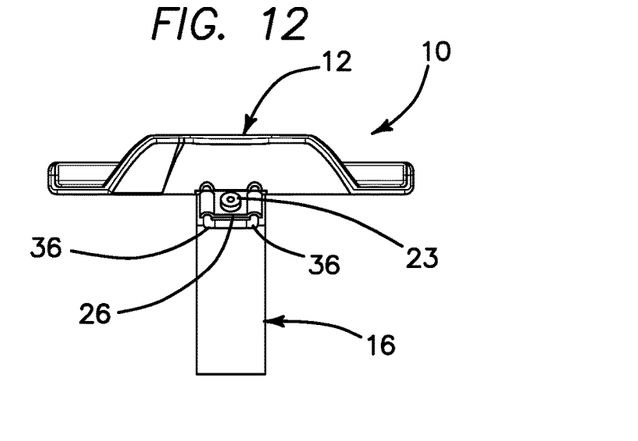
FIG. 12 is a rear view of the embodiment shown in FIGS. 9-11.

A cover plate 26, best shown in FIGS. 7 and 8, also forms a part of the clamp bracket 22, having a center aperture 28 for accommodating the dental screw and lock nut 23 and channels 30 for accommodating corresponding leg portions 24a, 24b of the bar center portion 24 (FIG. 6a). The respective leg portions 24a, 24b each include exterior notches 32, located at the point of contact of the leg portions 24a, 24b with respective channels 30 of the cover plate 26, while the channels 30 each have interior notches 34, which are adapted to engage with the exterior notches 32 to lock the tongue depressor 16 in place, in a manner similar to a zip-lock engagement feature. The respective notches 32, 34 are situated only at the point of contact between the pivoting/tension bar 18 and the cover plate 26. Aside from providing structural integrity, these engagement features protect the user in the event of structural failure caused by material fatigue and/or damage caused during cleaning or maintenance of the appliance. Additionally, the arrangement allows for modular replacement of both the tongue depressor and the pivoting/tensioning bar by a dental or orthodontic professional, without the necessity of rebuilding the entire appliance 10.

Unlike some prior art systems, in operation, the oral appliance 10 does not keep the tongue in a fixed position that restrains swallowing. Rather, it is made specifically to allow swallowing and comfort during sleep. The tongue begins to exert a small amount of forward tension on the tongue depressor 16 immediately upon application and insertion into the user's mouth. The appliance does not come into contact with the rear of the user's pharynx and therefore does not trigger the gag reflex while in use.

Moreover, the inventive appliance 10 does not require that the user be tethered to a machine, or the wearing of an uncomfortable and unsightly mask. It does not require an energy source to function. The appliance 10 is as easy to transport and maintain as a simple oral retainer or night guard appliance is. No additional attachments, cords, or removal are required when making occasional bathroom trips during the night.

When in use, the oral appliance 10 is also absolutely silent and void of the sound of a humming machine at night. Other than normal good oral hygiene, the appliance 10 does not require special cleaning procedures or cleaning agents.

Figures 13, 14:
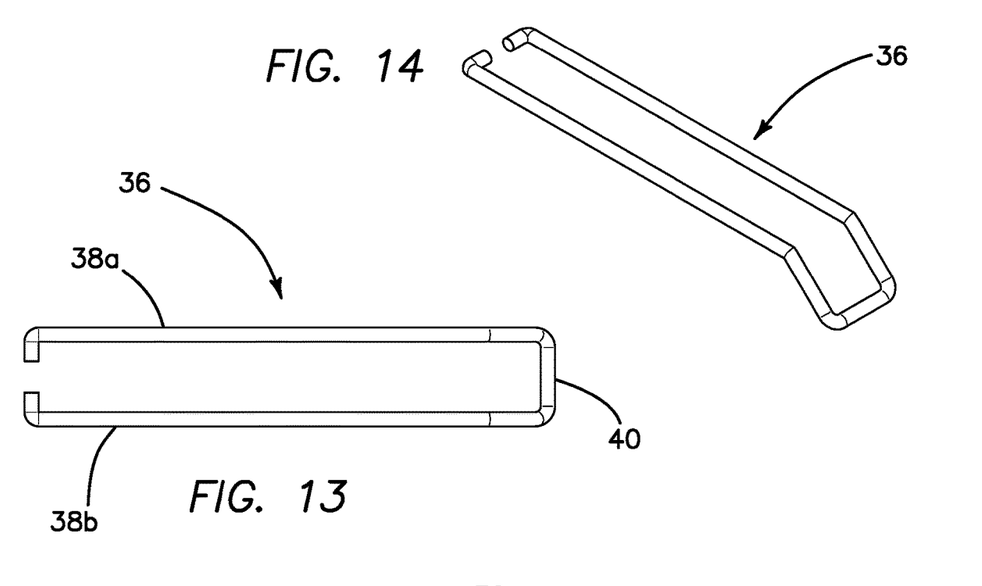
FIG. 13 is a top view of the center-mounted bar of the embodiment of FIGS. 9-11.
FIG. 14 is an isometric view of the center-mounted bar of FIG. 12.
Figure 15:
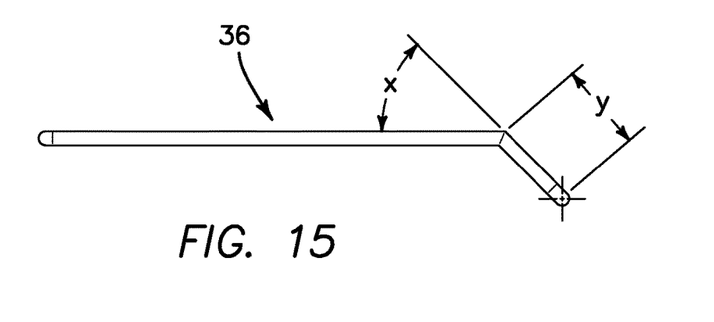
FIG. 15 is a plan view of the center-mounted bar of FIGS. 13-14.

A modified embodiment of the present invention is illustrated in FIGS. 9-15, wherein like elements are designated by like reference numerals. As shown in FIGS. 9-12, the appliance 10 of the second modified embodiment is similarly constructed in most ways as that of the appliance 10 of the embodiment of FIGS. 1-4, with the exception of the metal bar 18 of the first embodiment. This bar 18, which is "outside mounted" to each of the left and right rear ends of the frame 12, is absent in the modified embodiment, in favor of a "center mounted" corrosion resistant flexible metal bar 36, as particularly shown in FIG. 13. The use of this center-mounted bar 36 permits a spring-depressor function similar to that of the first embodiment, but also permits the bar 36 to be embedded in the frame 12 and tongue depressor 16, as shown in FIG. 13. As illustrated in FIGS. 13-15, the bar 36 comprises leg portions 38a and 38b, joined together by a bar center portion 40, which is configured for securement to the tongue depressor 16 using the clamp bracket 22. As shown in FIG. 15, the bar center portion 40 and adjacent portions of the leg portions 24a, 24b are disposed at an angle X relative to the remaining portions of the leg portions 24a, 24b, and this angled portion has a length Y. In one particular embodiment, Y is 0.394 inches, and the angle X is 45 degrees, though these values may vary depending upon design parameters. Flanges 42 at the other end of each leg portion 24a, 24b permit securement of the frame 12, typically by embedding the flanges 42 therein during a molding process. As noted, construction permits the appliance 10 to be manufactured using injection molding, and even 3D printing methods.

Figures 16, 17, 18:
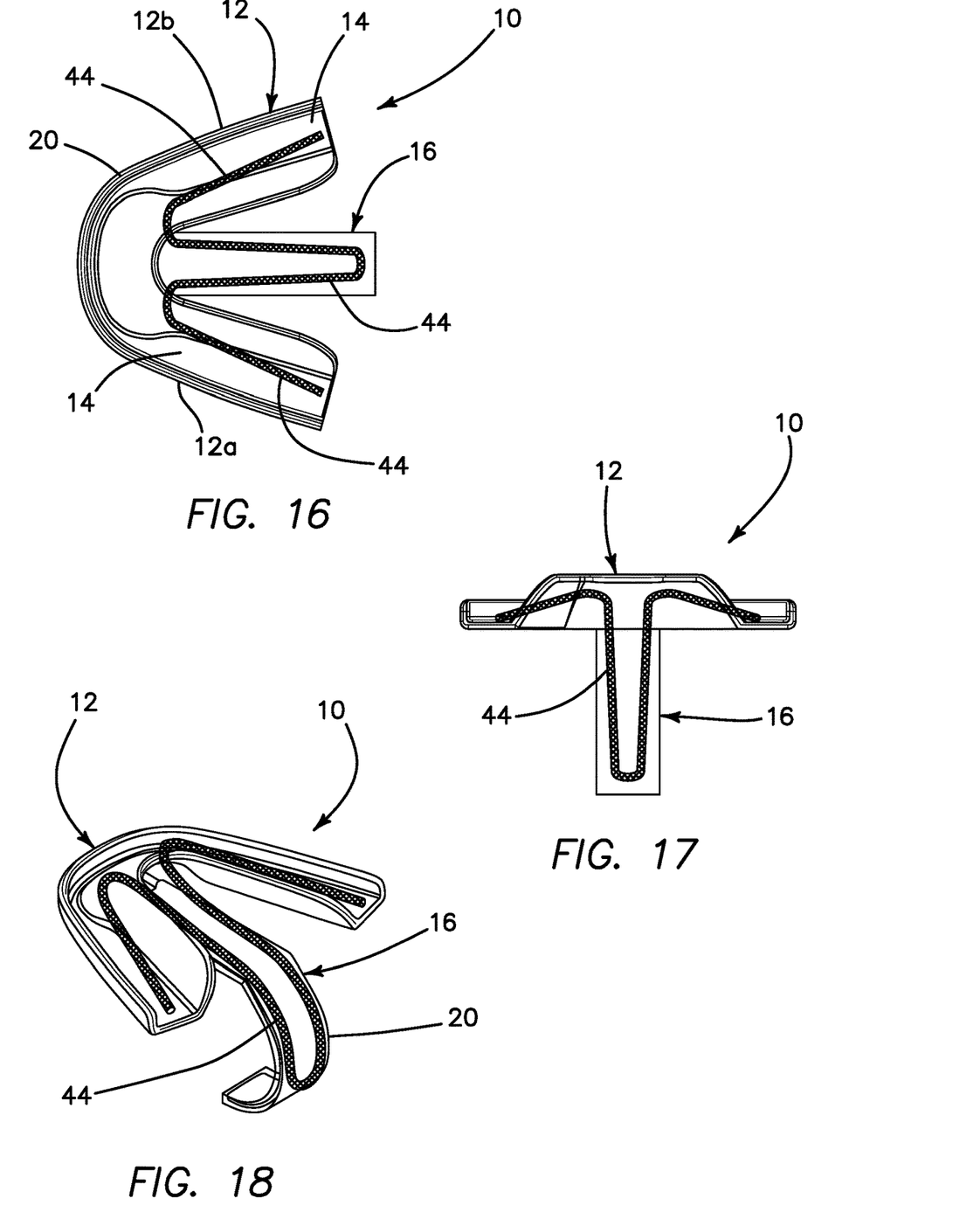
FIG. 16 is a top view of another exemplary embodiment of the present invention.
FIG. 17 is a rear view of the embodiment of FIG. 16.
FIG. 18 is an isometric view of the embodiment of FIGS. 16-17.

Still another modified exemplary embodiment of the inventive oral appliance 10 is illustrated in FIGS. 16-18, wherein like elements are designated by like reference numerals. The appliance 10 of this embodiment is similarly constructed in most ways as that of the appliance 10 of the embodiments disclosed in FIGS. 1-15, except that this embodiment is specifically designed to address the injection molding process. It is, therefore, designed as a solid state, one-piece device, with no moving parts. The tension bar 44 is embedded in the tongue depressor 16 and throughout the frame for support during the injection molding process, thereby producing a one-piece, solid state appliance with no moving parts.

More particularly, as in the prior embodiments, the appliance 10 comprises a frame 12 having a hard-exterior acrylic, or other similar suitable material, form, and a softer silicone-type inner lining 20 formed in the interior 14 of the frame 12, of a material that conforms to the user's teeth and natural bite at the point of contact when worn. The softer inner material 20 provides additional comfort while helping maintain the oral appliance securely and in place. The tongue depressor 16 extends directly from the acrylic frame, and is also encased with the softer silicone-type material noted above. The tongue depressor 16 may have a core constructed of a flexible plastic or silicone material. The soft silicone encasement can be replaced, as needed, due to normal use or if damaged.

The tension mechanism comprises tension bar 44 which is encased in the hard acrylic or other suitable material of the frame 12 during the injection molding or 3D printing process. The tension bar 44 begins in one end 12a of the frame 12, runs down one side of the tongue depressor 16, back up the other side of the tongue depressor 16, and then runs into the other end 12b of the frame 12. The encased tension/pivoting bar 44 provides additional structural integrity to the oral appliance 10. The tension/pivoting mechanism, as in the previous embodiments, allows the user to swallow at night without waking or discomfort, by gently returning the tongue to the forward position after the swallowing reflex, thus maintaining an open airway through the user's sleep. The tongue depressor 16 does not exert pressure on the user's tongue until occasional swallowing occurs. The tongue depressor 16 pivots on the tension bar 44 during swallowing, and then gently allows the tongue to return and rest on the tongue depressor 16. The combination of these features provides an unobstructed open airway for the user during sleep. The size and curvature of the tongue depressor and the pivoting/tension bar are determined by a dental professional according to the dental impressions taken, as in previously described embodiments.

The inventive device has been clinically tested and has proven more effective than the most commonly prescribed mandibular advancement appliances. Two separate sleep studies (polysomnography) on two different patients were conducted, and the results confirm the effectiveness of air flow and oxygenation during sleep. In each study, the first half of the night was spent without the inventive device. The second half of the night was spent with the inventive device in place in the user's mouth. The sleep studies showed that the inventive device controlled snoring and sleep apnea. The results showed a dramatic improvement in the AHI (Apnea Hypopnea Index). In both studies, the AHI was reduced by almost 90% with the inventive device in use, to a level well below 5 apneas or hypopneas per hour, which is considered to be "fully treated". In contrast, two different competitive mandibular advancement devices, in studies involving 183 and 75 patients, respectively, the AHI was only reduced to about 10 apneas or hypopneas per hour, with 40-53% considered fully treated. The results of these summaries are summarized in the following table.

| | AHI Baseline | AHI With Inventive Device | Percentage Improvement | Fully Treated (AHI <5) |
|---|---|---|---|---|
| Patient 1 | 19.9 | 2.4 | 88% | Yes |
| Patient 2 | 22.9 | 2.9 | 87% | Yes |

| Study | # of Patients | AHI Baseline mean +/− sd | AHI w/device Mean +/− sd | % Fully Treated (AHI < 5) |
|---|---|---|---|---|
| Mandibular Advancement Device 1 | 183 | 20.8 +/− 14.1 | 9.9 +/− 8.8 | 40% |
| Mandibular Advancement Device 2 | 75 | 30.6 +/− 20.0 | 10.5 | 53% |

While this invention has been described with respect to various specific examples and embodiments, it is to be understood that various modifications may be made without departing from the scope thereof. Therefore, the above description should not be construed as limiting the invention, but merely as an exemplification of preferred embodiments thereof.

What is claimed is:

1. A mouth appliance for maintaining effective airflow in a user's airway, comprising:
a frame adapted to engage the user's upper and lower teeth to retain the frame in a selected position in the user's mouth in accord with the user's natural bite, the frame having left and right portions thereof;
a flexible pivoting bar mounted to the frame, the flexible pivoting bar being comprised of a shape memory material;
a tongue depressor pivotally connected to and disposed beneath the pivoting bar and adapted to extend downwardly from and below the frame to a rear portion of the user's throat and to pivot on the pivoting bar to exert forward pressure directly on the user's tongue in the area of the user's soft palate, thereby facilitating comfort and ease in occasional swallowing, while providing airflow effectiveness to prevent the user from snoring and experiencing sleep apnea symptoms;
wherein first and second portions of the flexible pivoting bar extend along and from corresponding ones of the left and right portions of the frame, the first and second portions of the flexible pivoting bar each extending from the frame and being secured to the tongue depressor, distal portions of the flexible pivoting bar comprising a bar center portion having first and second leg portions.

2. The mouth appliance as recited in claim 1, wherein the first and second portions of the flexible pivoting bar are formed into their corresponding ones of the left and right portions of the frame.

3. The mouth appliance as recited in claim 1, wherein the first and second portions of the flexible pivoting bar are molded into their corresponding ones of the left and right portions of the frame.

4. The mouth appliance as recited in claim 1, wherein the flexible pivoting bar comprises Nitinol.

5. The mouth appliance as recited in claim 1, and further comprising a clamp bracket, the clamp bracket comprising channels for receiving the distal portions of the flexible pivoting bar therein and a fastener for securing the clamp bracket to the tongue depressor, to thereby secure the distal portions of the flexible pivoting bar to the tongue depressor.

6. The mouth appliance as recited in claim 1, wherein the first and second leg portions extend along a majority of a total length of the tongue depressor.

7. The mouth appliance as recited in claim 1, wherein the first and second leg portions extend along a small distal portion of a total length of the tongue depressor.

8. The mouth appliance as recited in claim 1, wherein the frame comprises a hard acrylic plastic, having a softer interior material and being encased by a soft silicone-type material.

9. The mouth appliance as recited in claim 1, wherein the tongue depressor comprises a metal alloy or a hard plastic, and is encased by a soft silicone-type material.

10. The mouth appliance as recited in claim 1, wherein the flexible pivoting bar is encased in the frame and in the tongue depressor and comprises portions thereof which extend along each of the left and right portions of the frame, and along a length of the tongue depressor.

11. A mouth appliance for maintaining effective airflow in a user's airway, comprising:
a frame adapted to engage the user's upper and lower teeth to retain the frame in a selected position in the user's mouth in accord with the user's natural bite, the frame having left and right portions thereof;
a flexible pivoting bar mounted to the frame, the flexible pivoting bar being comprised of a shape memory material;
a tongue depressor connected to the pivoting bar and adapted to extend to a rear portion of the user's throat and exert forward pressure directly on the user's tongue in the area of the user's soft palate, thereby facilitating comfort and ease in occasional swallowing, while providing airflow effectiveness to prevent the user from snoring and experiencing sleep apnea symptoms;
a clamp bracket, the clamp bracket comprising channels for receiving distal portions of the flexible pivoting bar therein and a fastener for securing the clamp bracket to the tongue depressor, to thereby secure the distal portions of the flexible pivoting bar to the tongue depressor;
first and second portions of the flexible pivoting bar extending along and from corresponding ones of the left and right portions of the frame, the first and second portions of the flexible pivoting bar each extending from the frame and being secured to the tongue depressor;
wherein the distal portions of the flexible pivoting bar comprise a plurality of notches, the plurality of notches being configured to engage with a plurality of notches disposed on a cover plate comprising a portion of the clamp bracket.

12. The mouth appliance as recited in claim 11, wherein the plurality of notches disposed on the distal portions of the flexible pivoting bar comprise exterior notches, and the plurality of notches disposed on the cover plate comprise corresponding interior notches.

13. A mouth appliance for maintaining effective airflow in a user's airway, comprising:
a frame adapted to engage the user's upper and lower teeth to retain the frame in a selected position in the user's mouth in accord with the user's natural bite, the frame having left and right portions thereof;
a flexible pivoting bar mounted to the frame, the flexible pivoting bar being comprised of a shape memory material;
a tongue depressor pivotally connected to and disposed beneath the pivoting bar and adapted to extend downwardly from and below the frame to a rear portion of the user's throat and to pivot on the pivoting bar to exert forward pressure directly on the user's tongue in the area of the user's soft palate, thereby facilitating comfort and ease in occasional swallowing, while providing airflow effectiveness to prevent the user from snoring and experiencing sleep apnea symptoms;

first and second portions of the flexible pivoting bar extending along and from corresponding ones of the left and right portions of the frame, the first and second portions of the flexible pivoting bar each extending from the frame and being secured to the tongue depressor;

the flexible pivoting bar being encased in the frame and in the tongue depressor and comprising portions thereof which extend along each of the left and right portions of the frame, and along a length of the tongue depressor, wherein the flexible pivoting bar comprises a single continuous piece, and the portions thereof which extend along each of the left and right portions of the frame comprise opposed ends of the flexible pivoting bar.

14. The mouth appliance as recited in claim 13, wherein the portions of the flexible pivoting bar which extend along the tongue depressor comprise a center length of the flexible pivoting bar, wherein the center length is curved so that two portions thereof are disposed in parallel along the length of the tongue depressor.

\* \* \* \* \*